United States Patent [19]

Hofstraat et al.

[11] Patent Number: 5,556,964
[45] Date of Patent: Sep. 17, 1996

[54] PROCESS FOR THE MANUFACTURE OF BUDESONIDE

[75] Inventors: Robert G. Hofstraat, Nijmegen; Petrus H. Raijmakers, Uden; Pieter Vrijhof, BX Berghem, all of Netherlands

[73] Assignee: Aktiebolaget Astra, Sodertalje, Sweden

[21] Appl. No.: 357,773

[22] Filed: Dec. 16, 1994

Related U.S. Application Data

[63] Continuation of Ser. No. 844,574, filed as PCT/SE90/00619, Sep. 27, 1990, published as WO91/04984, Apr. 18, 1991, abandoned.

[30] Foreign Application Priority Data

Oct. 2, 1989 [SE] Sweden .................. 89032197

[51] Int. Cl.⁶ .................................. C07J 73/00
[52] U.S. Cl. ............................. 540/63; 540/61
[58] Field of Search .................. 540/61, 63, 71

[56] References Cited

U.S. PATENT DOCUMENTS 3,077,471  2/1963  Fried et al. ................. 540/63
4,925,933  5/1990  Jakupovic et al. ........... 540/61

FOREIGN PATENT DOCUMENTS 0164636  12/1985  European Pat. Off. .
0054010   6/1992  European Pat. Off. .
543211    5/1985  Spain .
916996    1/1963  United Kingdom ........... 540/63
1429922   3/1976  United Kingdom .

OTHER PUBLICATIONS

Linan et al., Chemical Abstracts, vol. 106, 1987 Abstract 675739.

Chem. Abst. vol. 106, No. 9, p. 641, 67573 (Mar. 2, 1987).

Primary Examiner—Mukund J. Shah
Assistant Examiner—Pavanaram K. Sripada
Attorney, Agent, or Firm—White & Case

[57] ABSTRACT

The present invention relates to a novel process for the manufacture of (22 R,S)-16α, 17α-butylidenedioxy-11β, 21-dihydroxypregna-1,4-diene-3,20 dione (I) by reacting 11β, 16α, 17α 21-tetrahydroxypregna-1,4-diene (II) with butanal, $CH_3-CH_2-CH_2-CHO$, in acetonitrile in presence of p-toluenesulphonic acid as a catalyst.

3 Claims, No Drawings

PROCESS FOR THE MANUFACTURE OF BUDESONIDE

This application is a continuation of application Ser. No. 07/844,574, filed as PCT/SE90/00619, Sep. 27, 1990, published as WO91/04984 Apr. 18, 1991, now abandoned.

TECHNICAL FIELD

The present invention relates to a novel process for the manufacture of (22 R,S)-16α,17α-butylidenedioxy-11β,21-dihydroxypregna-1,4-diene-3,20-dione (budesonide)

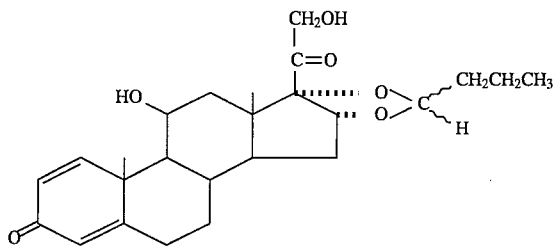

by reacting 11β,16α,17α,21-tetrahydroxypregna-1,4-diene-3,20-dione (16α-hydroxyprednisolone)

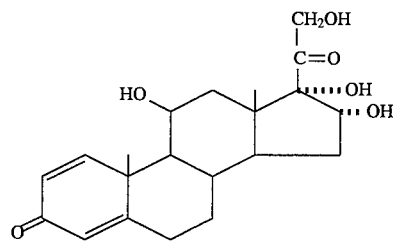

with butanal, $CH_3CH_2CH_2CHO$, in a solvent medium in the presence of an acid catalyst.

PRIOR ART

According to a previously known process disclosed in GB patent no. 1 429 922 Budesonide is manufactured by reacting 16α-hydroxyprednisolone with butanal in dioxane and with perchloric acid as a catalyst. The product is recovered by diluting the reaction mixture with methylene chloride, and neutralizing by washing with aqueous potassium carbonate and water evaporating the solvent followed by crystallization from ether/ligroine. The product was further purified by chromatography e.g. on Sephadex. The main disadvantages of dioxane are its skin penetrating and peroxide formation properties. Another disadvantage with this prior art process is perchloric acid, which is a strong oxidizing agent and the use of this catalyst results in a less selective reaction, which in turn makes the subsequent work-up and purification process complicated and expensive.

DISCLOSURE OF THE INVENTION

The object of the invention is to create a novel process, which gives a more selective reaction and a more simple and economic work-up and purification process.

This is achieved with the process according to the present invention, wherein the reaction is performed in acetonitrile with p-toluenesulphonic acid as a catalyst.

The combination of the less basic (compared to dioxane) solvent acetonitril and the weaker, i.e. non-oxidizing p-toluenesulphonic acid gives a more selective reaction, and also a more simple and exonomic work-up and purification process compared to the above discussed prior art process using dioxane and perchloric acid.

According to a preferred embodiment of the invention the reaction is stopped by the addition of water and adjustment of the Ph of the reaction mixture. This might be done by the addition of sodium hydrogen carbonate in water. The product then crystallizes. The crystals are filtered off, dissolved in methylene chloride and methanol and are then crystallized by the addition a suitable hydrocarbon, such as ligroine, hexane, cyclohexane or heptane, giving a crude product, which is then recrystallized in methanol/water to give pure budesonide.

The process according to the invention for the manufacture of budesonide thus consists of two steps.

Step 1. Budesonide crude

16α-hydroxyprednisolone is reacted with butanal in acetonitrile. p-Toluenesulphonic acid is added as a catalyst. The reaction mixture is diluted with water and aqueous sodium hydrogen carbonate. After cooling to 5°–15° C. the crystallized product is filtered off and washed with water. The wet or dried substance is then dissolved in methylene chloride. If the substance used is wet the water phase formed upon dissolution is removed. Methanol is added and the resulting crude budesonide is precipitated by the addition of ligroine or another suitable hydrocarbon (e.g. hexane, heptane or cyclohexane) and is then filtered off.

Step 2. Budesonide

The crude budesonide is dissolved in methanol at about 60° C. The solution is filtered through a closed filter and the product is crystallized by the addition of water. After cooling to 5°–20° C., filtration and washing with methanol/water the budesonide is dried in vacuum at 40°–45° C.

This process is simplified, more economic and less health hazardous compared to prior art processes.

WORKING EXAMPLE

The reaction is carried out in a nitrogen atmosphere. 15,4 g p-toluenesulphonic acid is dissolved into 200 ml acetonitrile. To the solution 50,0 g 16α-hydroxyprednisolone and 17.6 ml butanal are added. The temperature rises to 25° C. After 30 min most of the material is dissolved. Shortly thereafter the product starts to crystallize. After 3 hours the reaction is stopped by the addition of 75 ml aqueous saturated sodium hydrogen carbonate solution, whereupon the product crystallizes. The dried product is dissolved in methylene chloride and methanol and is crystallized by the addition of ligroine (b.p. 40–65) giving crude budesonide.

The crude budesonide product is recrystallized from methanol/water giving pure budesonide with isomer ratio A:B≈1:1 (HPLC), $[\alpha]_D^{25}$ 100.0° (c=0.2; $CH_2CL_2$); $M^+430$ (theor. 430.5)

We claim:

1. A process for preparing the compound (22 R,S)-16α, 17α-butylidene-dioxy-11B,21-dihydroxpregna-1,4-diene 3,20-dione (formula I)

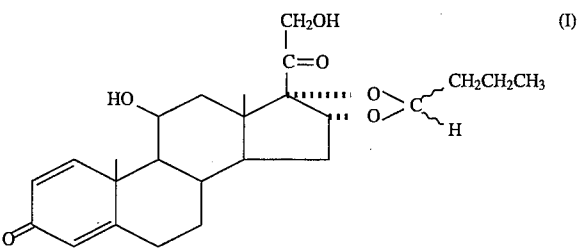

which compromises reacting the compound 11B, 16α, 17α, 21-tetrahydroxypregna-1,4-diene-3,20-dione (formula II)

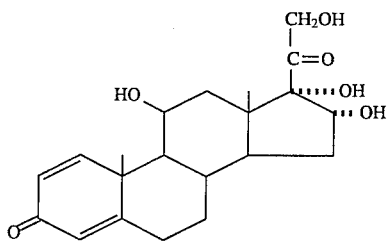

with butanal in acetonitrile in the presence of p-toluenesulfonic acid as a catalyst.

2. The process according to claim 1, wherein the reaction is terminated by adding water and adjusting the Ph of the reaction mixture.

3. The process according to claim 2 or which further comprises steps wherein crystals that are obtained upon termination of the reaction are filtered off, dissolved in methylene chloride and methanol and then crystallized by the addition of a suitable hydrocarbon selected from the group consisting of, ligroin, hexane, cyclohexane and heptane, giving a crude product, which is then recrystallized in methanol/water to give pure budesonide.

* * * * *